United States Patent [19]

Lahey et al.

[11] Patent Number: 4,780,117

[45] Date of Patent: Oct. 25, 1988

[54] TIME RELEASE COOLING SYSTEM

[76] Inventors: Thomas P. Lahey, 171 Johnstone Dr., San Francisco, Calif. 94131; Steven F. Abo, 1027 Acanto Pl., Los Angeles, Calif. 90049

[21] Appl. No.: 38,197

[22] Filed: Apr. 14, 1987

[51] Int. Cl.$^4$ ................................................ F25D 5/00
[52] U.S. Cl. .......................................... 62/4; 62/112; 126/263
[58] Field of Search ................ 62/4, 64, 114, 112; 126/263; 128/401–403

[56] References Cited

U.S. PATENT DOCUMENTS

| | | | |
|---|---|---|---|
| 3,804,077 | 4/1974 | Williams | 62/4 |
| 4,142,508 | 3/1979 | Watson | 126/263 |
| 4,203,418 | 5/1980 | Donnelly | 126/263 |
| 4,462,224 | 7/1984 | Dunshee et al. | 62/4 |

*Primary Examiner*—Henry A. Bennet
*Attorney, Agent, or Firm*—Bertram I. Rowland

[57] ABSTRACT

Extended period cooling packs are provided by employing reaction mixtures of coated particulate matter and a liquid reactant, where the liquid reactant reacts with the particulate matter in an endothermic reaction. The coating acts to slow the rate of reaction between the reactants, so as to extend the period of cooling.

19 Claims, 1 Drawing Sheet

TIME RELEASE COOLING SYSTEM

INTRODUCTION

Technical Field

Apparatus and compositions are provided for use in cold pack devices which maintain cooling for extended periods of time.

BACKGROUND

There is a frequent need to be able to reduce the temperature of a particular site on an animal or person, a reaction mixture, device, or the like. There are many instances where the normal coolants, such as ice, refrigerated cold packs, or the like, are not readily available or convenient. This may be particularly true where the cooling may be too severe, refrigeration may not be available, or storage of the coolant may be inconvenient. Recognizing this problem, cold pack devices have been developed which employ endothermic solubilization or reactions to provide cooling. By providing a portion of the reactants in one cell of the pack and the other portion in another cell, where the barrier cah be broken at will, cooling can be provided without the various problems associated with refrigeration.

While these devices find wide use, they suffer from many deficiencies. One of the problems of concern is te relatively short lifetime of the pack, so as to require a relatively large number of packs to maintain the cooling for an extended period of time. There is, therefore, a substantial interest in being able to improve such cold packs and greatly extend their useful lifetime.

Relevant Literature

U.S Pat. No. 3,977,202 describes a cold pack device employing an anhydrous salt and a water miscible organic liquid as separate components which are mixed to provide cooling. A large number of devices have been described in the literature which can provide for specific structures for cooling. See for example U.S. Pat. Nos. 4,596,250: 4,576,169: 4,537,18: 4,527,565: 4,522,640 4,427,010, which discloses the use of Xylite as a component of a cooling mixture: U.S. Pat. Nos. 4,404,820, which discloses a thin gel-like pad: 4,356,709, which discloses an ice cap: 4,344,303, which discloses a beverage container cooler: or 4,326,533, which discloses a coolant band; 4,240,436,which discloses a therapeutic cold pack: 3,950,158, which discloses a urea cold pack: 3,822,705, which discloses a refrigerant wrap for an animals limb: 3,804,077, which describes a hot or cold pack involving a gel: 3,763,622, which describes a pack involving a rupturable container: and 3,244,210, which describes a multi-ply plastic bag structure. U.S. Pat. No. 3,149,943 describes a pack having a granular material in one compartment and a liquid in the other compartment, where the two compartments have a particular structure to allow for mixing. These patents are not intended to be exhaustive, but merely illustrative of the various structures which may be employed, which disclosures are incorporated herein by reference.

SUMMARY OF THE INVENTION

Granular chemical reactants are coated with slow release coatings for use in refrigerant packs containing a liquid in which the coating is at least partially soluble or swellable. Upon mixing of the granular coated material and the liquid, an endothermic reaction occurs resulting in cooling. The cooling period can be greatly extended by selection of the coating, the thickness, and the nature of the liquid.

DESCRIPTION OF THE SPECIFIC EMBODIMENTS

Figure 1:
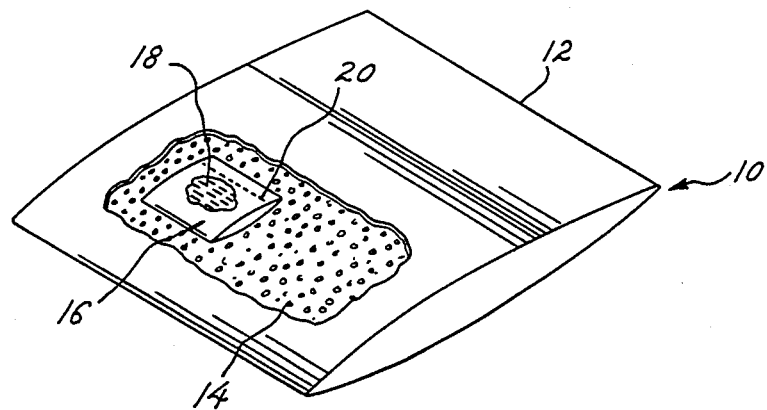
FIG. 1 is a perspective view of one embodiment of a cold pack according to this invention.

Apparatus and compositions are provided which provide convenient cold packs which have extended cooling lifetimes. By employing these packs, a relatively substantially constant temperature may be maintained below ambient temperatures for an extended period of time. The packs can maintain at least about a 10° C. reduction in temperature for about five minutes, usually for about ten minutes, and frequently 20 minutes or longer, including 6 hours or longer, depending upon the particular combination of reagents or reactants and size of the pack.

The reactants will involve a coated or encapsulated solid which reacts with a liquid in an endothermic reaction. The solid will be present as particles of from about 10 to 500 U.S. mesh, more usually from about 20 to 200 U.S. mesh, preferably from about 50 to 200 U.S. mesh. The particles employed may be approximately all the same size, that is, within about 20% of the average diameter, or mixtures of particles may be employed, ranging from particles at either end of the range with the range of particles differing by more than 200% in diameter. By varying the size distribution of the particles, one may also vary the temperature profile of the cold pack, although the size of the particle will be a substantially less significant factor than the nature of the encapsulating coating.

The particle may be of any material which can be used to react with a liquid to result in an endothermic reaction to provide the desired temperature reduction. A wide variety of materials are available, such as inorganic salts, particulary ammonium salts, more particularly ammonium sulfate and ammonium nitrate, organic materials, such as sugars, e.g. Xylite, and the like.

These materials may be coated with a wide variety of slowly soluble, insoluble or swellable substances, particularly polymeric substances which will have a reasonably slow rate of penetration, e.g. solution or swelling in the liquid medium. Thus, the substance is selected to reduce the rate at which the particulate reactant will dissolve. The substance is also selected to have a low heat of reaction or solution with the liquid. Various substances may be selected which have measurable rates of penetration in a solvent, such as water or alkaline water. In discussing substances, one must also consider the nature of the solvent which is used in conjunction with the substance.

With polymers, the polymers may be addition polymers, condensation polymers, synthetic, naturally occurring, or combinations thereof. One group of polymers of particular interest are acidic polymers having carboxyl groups. The polymers will generally have a KOH number (mg KOH/gm polymer) in the range of about 50 to 200, more usually in the range of about 100 to 195, particularly in the range of 165 to 195. The acidic polymers may be employed as the acid, salt, e.g. sodium, or combination thereof.

Illustrative addition polymers include acrylic and methacrylic polymers, which may be homo- or copolymers, where the other monomer may be an ester or amide of acrylic or methacrylic acid, or a different monomer, such as an olefin, e.g. ethylene, styrene, etc., or polymers of maleic or fumaric acid, such as copolymers with styrene, vinyl halides, etc. Alternatively, phenolic polymers may be employed, such as hydroxystyrene, which polymers may be homopolymers or copolymers. Another category of polymers are cellulosic polymers, such as methylcellulose, hydroxyethylcellulose, carboxymethylcellulose, etc. The carboxy groups may be partially esterified or amidified with alkanols, ammonia or amines, where the organic groups will be from about 1 to 6 carbon atoms.

Illustrative condensation polymers include polyurethane, e.g. biphenylenediisocyanate or polytolyleneisocyanate with polyols, e.g. ethylene glycol, diethylene glycol, etc.: phenol-formaldehyde resins, particularly substituted phenols, such as cresols, polar organic solvent soluble polyesters, e.g. polyterephthalates, polyalkylene oxides, polyamides, etc. particularly those soluble or swellable in oxo solvents such as acetone and MEK. Also, waxes may find use, that is hydrocarbons, alkanols and the like of at least 14, usually at least about 16 carbon atoms, and up to 60 carbon atoms or more or mixtures thereof.

The amount of polymer which is coated onto the pellets will vary widely, depending upon the rate of dissolution desired. The coating substance will be at least about 0.2 weight percent of the particulate reactant and not more than about 10 weight percent, more usually not more than about 5 weight percent, generally ranging from about 1 to 5 weight percent based on the particulate reactant.

The particles may be coated by any convenient means spraying, shaking, dipping, mixing, or the like. The means chosen should be reasonably certain to ensure that substantially all of the solid particles are completely coated with the polymer with a relatively even coating. Of particular interest is the use of a volatile solvent for the polymer in which the particles are at least substantially insoluble and rolling the particles, while evaporating the solvent. Clearly, various solvents may be employed with the various polymers, particularly oxygenated solvents, such as alkanols of three or greater carbon atoms, ketones of three or greater carbon atoms, esters of five or greater carbon atoms, and the like, usually not being more than about 10 carbon atoms. The concentration of the polymer in the solvent may vary, generally being at least about 5% and not more than about 95%, usually not more than about 90%, conveniently ranging from about 10% to 75% by weight of solution. The polymer concentration is not critical, depending on viscosity of the solution, thickness of the coating, etc.

With some polymers from about 0 to 15 wt % of the coating composition will be solvent and coatings will be carried out at elevated temperatures ranging from about 30° to 150° C., usually 40° to 150° C., where with molten polymers the temperature range will be about 80° to 150° C., while for partially solvent softened polymers the temperature range will be about 40° to 80° C.

Other materials may be included in the coating solution, such as anticaking materials, antifoaming agents, etc.

The liquid reactant with the acidic polymers is conveniently an alkaline aqueous solution, where the polymers are selected so as to have low solubility at a pH of 7 or below and a substantially enhanced solubility at a pH of 7.5 or higher, generally in the range of about 7.5 to 10. Thus, the rate of solution can be controlled in part by varying the pH of the aqueous media.

The amount of particulate matter employed in relation to the amount of liquid will generally be at least about 5% by weight and may be as high as 100% by weight, generally ranging from about 5-50% by weight of the liquid reactant. The amount of water used and the pH of the water can be determined empirically, depending upon the amount of cooling desired and the period of time in which the cooling should be maintained under standarized conditions. By varying the amounts of coating, one can define specific specifications as to the amount of cooling which will be obtained by the defined reagents.

The reactants will be introduced into a pouch or other container, so as to be maintained separately, until mixing is desired. Various containers can be designed for a variety of purposes as previously indicated, when discussing the relevant literature. The simplest container may be a plastic pouch in which is placed the coated particles and a small sealed bag containing the liquid, which bag can be easily ruptured. When mixing is desired, one need only rupture the internal bag to provide for release of the liquid and mixing of the particle with the liquid.

Alternatively, one could have a bag with two compartments, employing a clip to seal one compartment from the other, a groove and ridge molded across the pouch, so as to form a seal and define two separate compartments, an internal valve, which can be turned from an open to a closed position, or the like.

There may be two or more compartments, or there may be a plurality of compartments having liquids having different properties, for example, different pHs, or a plurality of compartments having particles having different properties, such as coating thickness, coating composition, or the like. In addition, various thickening agents or gels may be included which act to form a pouch which may be shaped in accordance with the conformation of the site being cooled, so as to provide for a better fit with the site. The subject reagent system can be used with the wide variety of structures which have been reported in the relevant literature.

For further understanding of the invention, the figures will now be considered.

In FIG. 1 is depicted in three dimensions, a pouch 10 which is sealed at the top at line 12. The particles 14 and a bag 16 are introduced into the pouch followed by sealing along line 12. The bag 16 contains the liquid reactant 18 and has tearline 20. Tearline 20 can be gripped from the outside and pulled so as to open the bag 16 and release its contents. In this manner, mixing of the liquid with the particles is inhibited until needed.

Figure 2:
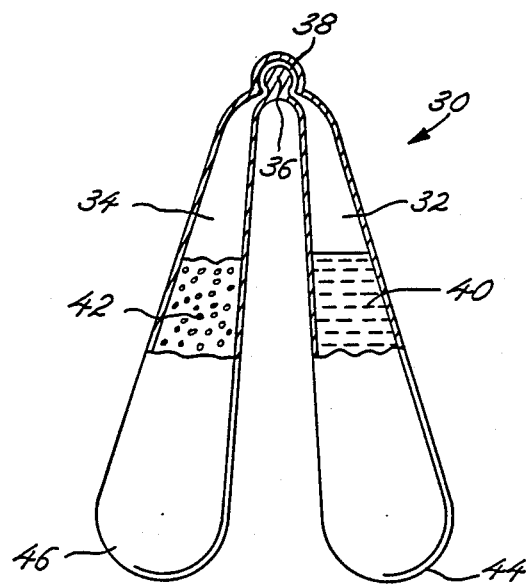
FIG. 2 is a front elevational view of a second embodiment of a cold pack according to this invention.

An alternative to the above pouch is depicted in FIG. 2. In FIG. 2, the pouch 30 has two compartments 32 and 34. The compartments are sealed one from the other by ridge 36 which is held snugly in groove 38, where the ridge and groove run the width of pouch 30. In compartment 32 is the liquid reactant 40, while the particulate reactant 42 is present in compartment 34. The compartments may be filled by having the compartments initially open at sites 44 and 46 respectively, introducing the reactants into the appropriate compartments, while maintaining the ridge and groove in the sealed position and then sealing the compartments by any convenient means, such as plastic heat sealing, adhesive, or the like. When mixing of the reactants is desired, the ridge 38 may be pulled out of the groove 36, so as to allow for mixing of the reactants.

In order to demonstrate the subject invention the following experiments were carried out.

The time-release particles were prepared as follows. A methyl ethyl ketone solution of Scripset 540 polymer (1.8 g SS540 in 8.2 g MEK) was added to 80 g of 100 mesh ammonium nitrate pellets and placed on a Rotovap. Vacuum was applied slowly to prevent foaming and the solvent slowly removed while rotating the particles and liquid to provide for a smooth even coating of the particles. While some agglomeration was noted, the agglomeration could be readily broken up by tapping.

To test the effect of the presence of the polymeric coat, the following study was carried out. A series of two 16-oz Styrofoam cups with lids are employed. A 1/16 inch hole is put in the top of the lid to allow for the placement of a thermocouple wire. Two magnetic stir bars of equal weight and size are placed in the cups. Fifty ml of deionized water or deionized water at an elevated pH resulting from the addition of sodium carbonate, all at ambient temperature, is added to each cup.

A sample of material to be evaluated for its time release cooling characteristics is weighed and the percent active ingredient is calculated by knowing the percent of the coating agent and calculating the difference. A sample of active ingredient equal in weight to the weight of active ingredient alone in the time release sample is weighed. The two systems are placed on top of a magnetic stirring device and the temperature recorded simultaneously. The samples are added and the temperatures recorded to determine the effect of the time release agent on the cooling of the solutions. The areas under the curve should be equal, but the slopes of the curve will indicate the rate of cooling and the effect of time release.

The temperature is recorded with a Perkin Elmer dual pen recorder with 50 mV full scale deflection (100° C.,). 10 g of ammonium nitrate pellets otained from a Kwik Kold pack are added with stirring and the temperatures observed for ten minutes or until a constant temperature rise is observed. In the other container 10.23 grams of polymer coated pellets are added, where the solutions are varied between deionized water, water containing 0.5 g sodium carbonate, and water containing 0.1 g sodium carbonate.

It was observed that the time release provided an approximately ten times greater period of cooling than the uncoated pellets as evidenced by the lesser negative slope of the cooling curve. The greater the base strength, the shorter the reduced temperature period was observed.

The following table indicates the results.

TABLE 1

TIME RELEASE COATINGS FOR USE ON AMMONIUM NITRATE PELLETS IN A TIME RELEASE COOLING SYSTEM

| Polymer type and percent coating weight/weight | Initial temp of $H_2O$, °C. | Final temp of $H_2O$ °C. | Cooling rate, °C./min |
|---|---|---|---|
| Scripset 540, 2.3% | 25.0 | 16.5 | −1.7 |
| Scripset 540 10% in B-66, 8% coating on pellets | 25.0 | 17.0 | −0.3 |

TABLE 1-continued

TIME RELEASE COATINGS FOR USE ON AMMONIUM NITRATE PELLETS IN A TIME RELEASE COOLING SYSTEM

| Polymer type and percent coating weight/weight | Initial temp of $H_2O$, °C. | Final temp of $H_2O$ °C. | Cooling rate, °C./min |
|---|---|---|---|
| B-66, 8% | 25.0 | 20.0 | −0.08 |

Scripset 540 is a mixed methyl and isobutyl partial ester of styrene-maleic anhydride copolymer which was obtained from Monsonto Company.
B-66 is an acrylate binder commercially available from Rohm and Haas Company.
The Scripset 540 coating (2.3%) was prepared by adding a soulution of Scripset 540 in methyl ethyl ketone to the ammonium nitrate pellets and placing the flask on a roto-evaporatory device to remove the solvent while coating the pellets.
The 10% Scripset 540 in B-66 coating (8% weight/weight), and the 8% B-66 coating was prepared by adding a 50% solution of the polymer (blend) to the ammonium nitrate pellets and mixing in a sealed jar rolled on its side. The coated pellets were then poured out of the jar and allowed to air dry on a polyester sheet.

The next study involved the use of the condensation polymer Novolac as the coating. The following table indicates the results.

TABLE 2

TIME RELEASE COATINGS FOR USE ON AMMONIUM NITRATE PELLETS IN A TIME RELEASE COOLING SYSTEM

| Polymer type and percent coating weight/weight | Initial temp of $H_2O$, °C. | Final temp of $H_2O$ °C. | Cooling rate, °C./min |
|---|---|---|---|
| CRJ-406, 5% | 25.0 | 13.3 | −7.6 |
| CRJ-406, 7% | 25.0 | 14.1 | −6.3 |
| m-Cresol Novolac | 25.0 | 14.5 | −3.2 |

CRJ-406 is an ortho-cresol Novolac obtained from Schenectady Chemicals, New York.
m-cresol Novolac was made using 0.8 equivalents of paraformaldehyde in the presence of sulfuric acid catalyst.

It is evident from the above results, that greatly improved performance is achieved by employing encapsulated or coated particles for use in extended period cold packs. In this manner, a single pack can provide reduced temperature for long periods of time, rather than requiring repeated replacement of the pack. In addition, the packs can be used more efficiently and provide a variety of economies.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An extended lifetime cold pack comprising:
   a container having first and second compartments separated by a barrier capable of being opened to provide communication between said first and second compartments:
   said first compartment containing solid reactant particles coated with a reaction delaying penetrable coating, said coating being at least partially soluble or swellable in a liquid reactant; and
   said second compartment containing said liquid reactant which reacts with said solid reactant in an endothermic reaction.

2. A cold pack according to claim 1, wherein said solid reactant is soluble in said liquid reactant and has a negative heat of solution.

3. A cold pack according to claim 1, wherein said solid reactant is an inorganic salt.

4. A cold pack according to claim 3, wherein said inorganic salt is ammonium salt.

5. A cold pack according to claim 1, wherein said penetrable coating is a polymer coating, and said liquid reactant is an aqueous alkaline solution in which said particles and said polymer are soluble.

6. An extended lifetime cold pack comprising:
a container having first and second compartments separated by a barrier capable of being opened to provide communication between said first and second compartments:
said first compartment containing solid ammonium salt reactant particles coated with a reaction delaying carboxylic acid containing polymer coating, said coating being at least partially soluble in an aqueous alkaline liquid reactant; and
said second compartment containing said aqueous alkaline liquid reactant which reacts with said solid reactant in an endothermic reaction.

7. A cold pack according to claim 6, wherein said ammonium salt is ammonium nitrate or sulfate and said polymer has a KOH number in the range of 50 to 200.

8. A cold pack according to claim 7, wherein said KOH number is in the range of 165 to 195 and said polymer is a styrene-maleic anhydride copolymer.

9. A cold pack according to claim 7, wherein said KOH number is in the range of 165 to 195 and said polymer is an acrylic or methacrylic polymer or copolymer.

10. A cold pack according to claim 6, wherein said particles have a size in the range of 10 to 500 U.S. mesh.

11. A cold pack according to claim 10, wherein said particle size is in the range of 50 to 200 U.S. mesh.

12. An extended lifetime cold pack comprising:
a container comprising a sealed pouch and a rupturable sealed bag within said sealed pouch:
said pouch containing solid ammonium salt reactant particles coated with a reaction delaying carboxylic acid containing polymer coating, said coating being at least partially soluble in an aqueous alkaline liquid reactant; and
said bag containing said aqueous alkaline liquid reactant which reacts with said solid reactant in an endothermic reaction.

13. Coolant particles comprising an ammonium salt having a negative heat of solution in water coated with a carboxylic acid containing polymer having a KOH number in the range of 50 to 200, wherein said polymer is from about 0.2 to 10 weight percent of said particles.

14. Particles according to claim 13, wherein said ammonium salt is ammonium nitrate or sulfate.

15. Particles according to claim 14, wherein said particles are of a mesh size in the range of 50 to 200 U.S. mesh.

16. Particles according to claim 14, wherein said polymer is a styrene-maleic anhydride copolymer.

17. Particles according to claim 14, wherein said polymer is an acrylic or methacrylic polymer or copolymer.

18. Particles according to claim 14, wherein said polymer is a cresol-formaldehyde polymer.

19. A method for cooling a site at a temperature greater than about ambient temperature, said method comprising:
combining particles according to claim 13 with an aqueous solution in a container conforming to said site to be cooled; and
applying said container to said site,
whereby the endothermic reaction of said particles with said solution lowers the temperature of said solution below ambient temperature by at least 10° C. for at least 5 minutes.

* * * * *